United States Patent
Barth et al.

(10) Patent No.: US 7,844,474 B2
(45) Date of Patent: Nov. 30, 2010

(54) SYSTEM AND METHOD FOR THE CREATION OF A VIRTUAL OBSERVATION AND ACCESS CHANNEL IN MEDICAL 3D IMAGES

(75) Inventors: Karl Barth, Höchstadt (DE); Gerd Wessels, Effeltrich (DE)

(73) Assignee: Siemens Aktiengesellschaft, Munich (DE)

( * ) Notice: Subject to any disclaimer, the term of this patent is extended or adjusted under 35 U.S.C. 154(b) by 1851 days.

(21) Appl. No.: 10/897,674

(22) Filed: Jul. 23, 2004

(65) Prior Publication Data

US 2005/0058326 A1    Mar. 17, 2005

(30) Foreign Application Priority Data

Jul. 25, 2003  (DE) ............... 103 34 074

(51) Int. Cl.
*A61B 5/00* (2006.01)
*G06F 19/00* (2006.01)
(52) U.S. Cl. ......................................... 705/3
(58) Field of Classification Search ............... 600/102, 600/426, 427; 705/2, 3
See application file for complete search history.

(56) References Cited

U.S. PATENT DOCUMENTS

| | | | |
|---|---|---|---|
| 5,623,586 A | | 4/1997 | Höhne |
| 5,876,325 A | * | 3/1999 | Mizuno et al. ............... 600/102 |
| 6,256,529 B1 | * | 7/2001 | Holupka et al. ............. 600/427 |
| 6,470,207 B1 | * | 10/2002 | Simon et al. ................. 600/426 |
| 7,171,255 B2 | * | 1/2007 | Holupka et al. ............. 600/427 |

OTHER PUBLICATIONS

"A Novel Mechatronic Tool for Computer-Assisted Arthoroscopy," Dario et al, IEEE Trans. on Information Technology in Biomedicine, vol. 4, No. 1, Mar. 2000, pp. 15-29.
"Stereo display of Nested 3D Volume Data Using Automatic Tunnelling," Hubbold et al, P. Roc. Electronic Imaging '99, Conf. on Stereoscopic Displays and Applications, vol. 3639, Jan. 1999, pp. 200-207.
Interactive Display and Analysis of 3D Medical Images, Robb et al, IEEE Trans. on Medical Imaging, vol. 8, No. 3, Sep. 1989, pp. 217-226.

* cited by examiner

*Primary Examiner*—Gerald J. O'Connor
*Assistant Examiner*—Trang Nguyen
(74) *Attorney, Agent, or Firm*—Schiff Hardin LLP

(57) ABSTRACT

In a system for the producing and displaying a virtual access channel in medical images, having a computer with a monitor, and a position and orientation-capturing operating unit and a method for producing and displaying such a virtual access channel in medical 3D images, the computer contains a preoperatively obtained 3D data record of a patient to be examined and can display this as a 3D image and is connected with the operating unit such that a virtual optical channel of the 3D data record is excised from the data record based on a registration between the operating unit and the data record as well as based on different channel parameters, and is displayed on the monitor of the computer.

23 Claims, 3 Drawing Sheets

FIG 2A
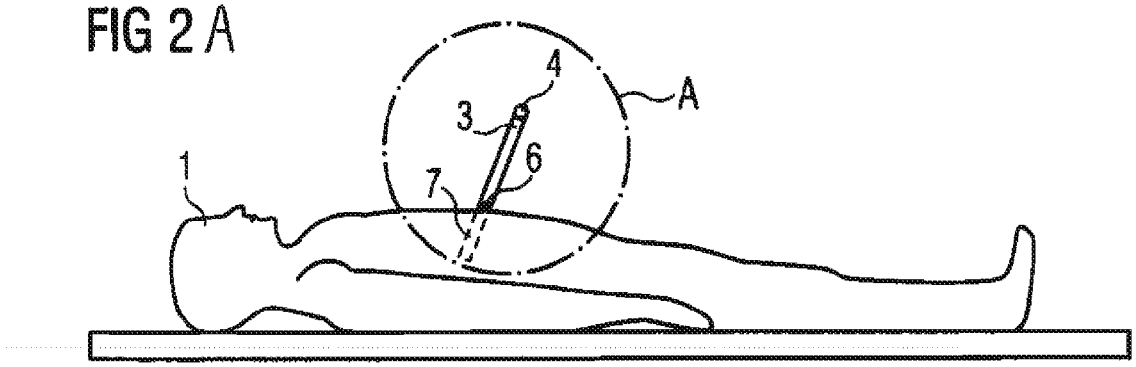
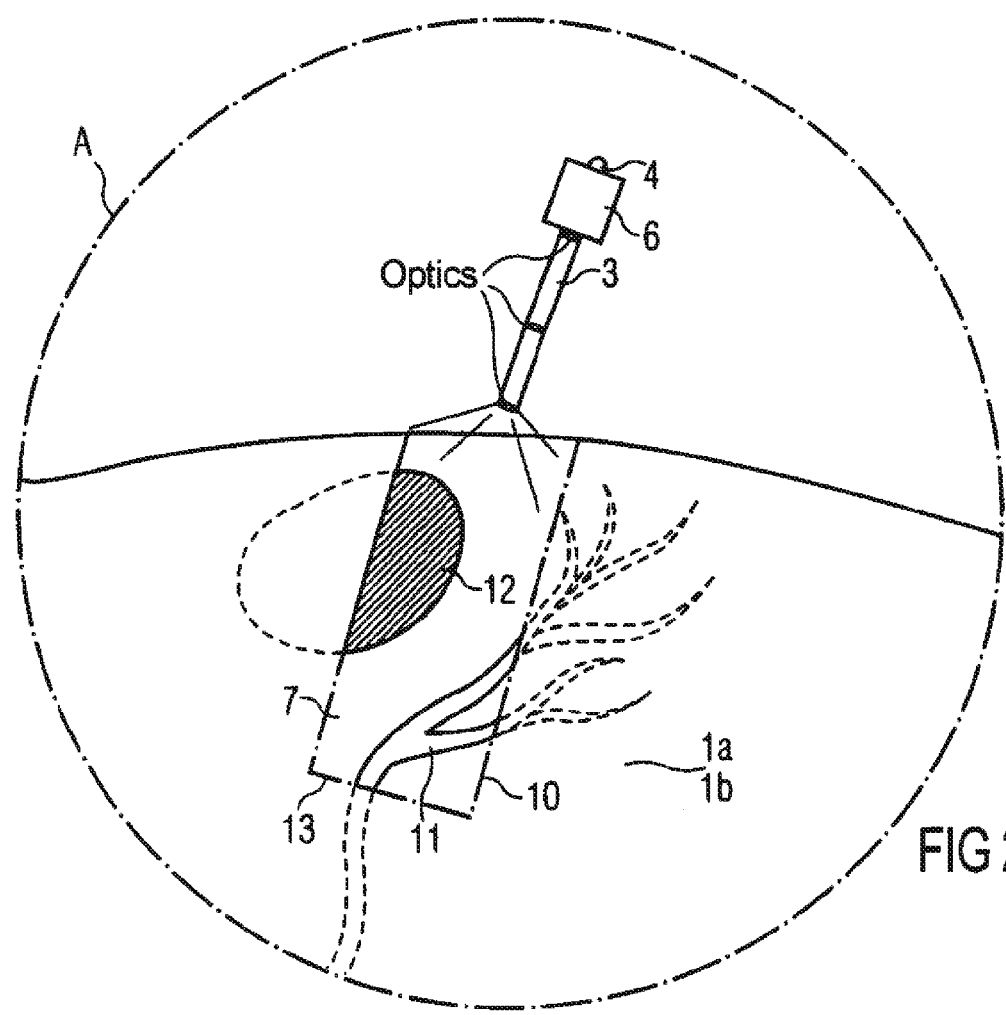
FIG 2B

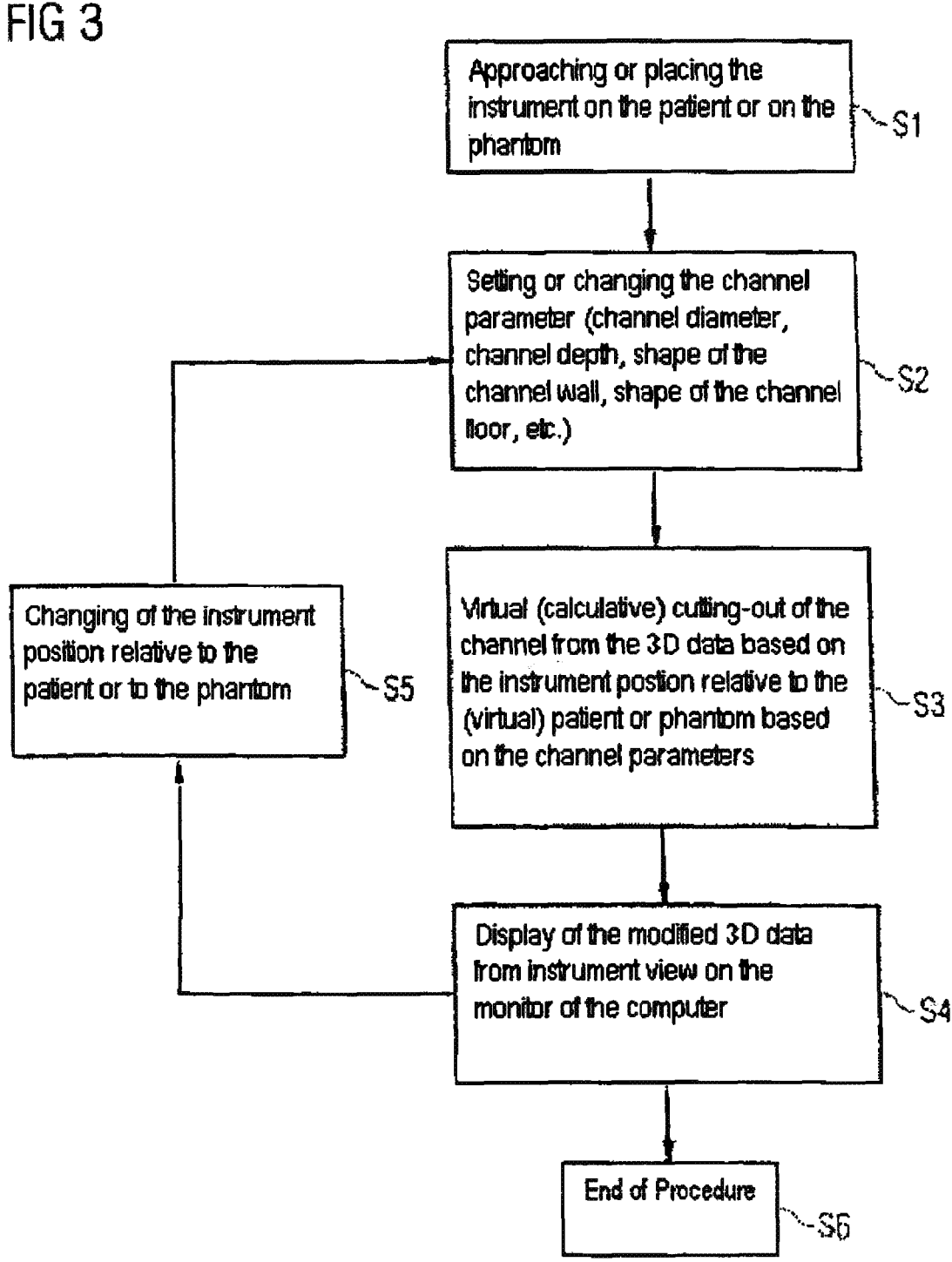

SYSTEM AND METHOD FOR THE CREATION OF A VIRTUAL OBSERVATION AND ACCESS CHANNEL IN MEDICAL 3D IMAGES

BACKGROUND OF THE INVENTION

Field of the Invention

The present invention relates to a procedure for the creation of a virtual access channel in a 3D image of a patient to be examined, obtained preoperatively or intra-operatively with any imaging modality. The invention serves in particular to plan and support minimally invasive medical procedures.

Examinations and treatments of patients increasingly are undertaken in a minimally invasive manner, i.e. with as little patient traumatization as possible. For example, diagnostics or an operation in so-called "key-hole surgery" are performed with endoscopes or laparoscopes. Endoscopes and laparoscopes are inserted into the examination area of the patient via a small body opening and deliver predominantly optical images (video images), and sometimes other images e.g. ultrasound scans "on site" (e.g. the laparoscopic ultrasound). The endoscope in particular allows examination of naturally accessible body cavity spaces such as e.g. esophagus, intestines, or within in the framework of a small puncture for examining blood vessels. An endoscopic examination of the intestines is known as colonoscopy or coloscopy.

In this context, for procedure planning and for an even less invasive diagnosis, there are the options of virtual endoscopy, virtual colonoscopy, as well as virtual laparoscopy. This concerns representing actual existing body cavity spaces based on 3D images and simulated movement therethrough. This type of procedure is also called the "fly-through technique." The 3D images underlying this procedure normally are acquired with high-resolution imaging procedures, e.g. with computed tomography (CT), magnetic resonance tomography (MRT), positron emission tomography (PET), nuclear-medicine imaging procedures, (C-arm) X-ray procedures or ultrasound (US). In current virtual examination procedures, the primary concern is to spatially represent the organ morphology. Such a representation takes place two-dimensionally for a selected layer within the framework of the known multiplanar reformatting (MPR) procedure, or three-dimensionally within the framework of MIP (maximum intensity projections), in e.g.—medium-filled vessels are highlighted. A fly-through usually takes place based on a 3D SSD (shaded surface display) representation or a 3D VR (volume rendering) representation. This requires in general a special segmenting, e.g. of the vessel walls, before a clear representation is possible in the fly-through. This segmentation or (inner) surface representation goes beyond the generic segmentation of the SSD procedure. Even with VR-similar fly-through representations, a type of segmentation is necessary, if only to insure that the vessel walls are not penetrated in this virtual flight.

From the perspective of a surgical user, there is a desire to be able to avoid a complicated segmentation and to use a more dynamic virtual procedure.

SUMMARY OF THE INVENTION

An object of the present invention is to provide a system and a procedure for virtually representing the inside of the body, which enable a more flexible representation and do not have to require orientation to the absolutely correct recognition of anatomical conditions, which is not absolutely reliable in today's state of computed technology.

This object is achieved according to the invention by a system for the creation of a virtual access channel in medical 3D images is claimed, having a computer with a monitor, and a position and orientation-capturing operating unit, wherein the computer contains a preoperatively obtained 3D data record of a patient to be examined that can be represented as 3D image, and wherein the computer is connected with the operating unit for, based on a registration between the operating unit and the 3D data record as well as based on different channel parameters, excising a virtual, optical channel of the 3D data record displaying it on the monitor of the computer.

In accordance with the invention, a data selection procedure is implemented in the computer that dynamically fades data in the area of the actual virtual position of the operating unit in the 3D data record, for example "laterally and in front of the instrument" and thus creates the named virtual observation and access channel.

Generally, the operating unit according to the invention represents a mechanically articulated system or a navigation system or a rod-shaped instrument with a navigation sensor or with an optical or magnetic marking or a standard computer input system.

The representation of the virtual channel can be influenced via the operating unit. In the simplest case, the operating unit, as a standard computer input system, is formed by corresponding function keys on a computer keyboard, a computer mouse or a 3D stylus. A modification of the 3D stylus can take place by the simulation of a medical instrument like e.g. a laparoscope. It is easy to implement a local registration and a constant position capture based on the 3D data record and thus the 3D representation with a 3D-stylus-like 3D input device.

By operation with the mouse, the 3D stylus, or using optical or magnetic navigation, the virtual channel moves and thereby allows a quick search for an optimal view or a search for an optimal, truly minimally invasive access channel for the subsequent actual intervention, or for laparoscopy, stereotaxis or brachytherapy.

The previously recorded 3D data record preferable is recorded with a high-resolution imaging modality e.g. with magnetic resonance tomography, computed tomography, ultrasound, positron-emission tomography or nuclear-medicine procedures.

In accordance with the invention, the virtual excision takes place as an automatic calculation by means of an algorithm on the computer.

The channel parameters preferably pertain to the channel diameter, the channel depth, the shape of the channel wall as well as the shape of the channel base.

The system in accordance with the invention enables the portrayal of a medical instrument in the virtual channel.

The movement of the virtual channel and the displayed instrument preferably take place independently of each other based on a second position and orientation-capturing operating unit.

The mechanically articulated system can be a robot arm.

Via the mechanics of the articulated system as well as based on a tissue thickness map of the 3D data record, haptic feedback can take places, via which the user obtains a feeling for the tissue to be penetrated or cut through or not to be damaged in the subsequent actual intervention. For example, large blood vessels should not be compromised in any way, but should be carefully pushed to the side.

Within the framework of an optimized and planned operative intervention, it can be advantageous in certain circumstances to show the images of the virtual channel coupled with corresponding intra-operative real images. Coupled means: next to or on top of each other or fused.

In accordance with the invention, the intra-operative real images are obtained with laparoscopic, colonoscopic, or endoscopic procedures and/or with ultrasound.

The above object also in accordance with the invention, by a method for the creation of a virtual access channel in medical 3D images including the steps of virtually excising an optical channel based on a previously recorded 3D data record of a patient, based on set channel parameters as well as based on a position and orientation-capturing operating unit registered relative to the 3D data record, representing the virtual channel on the monitor of a computer, and repeating the virtual excision and the representation (iteratively) until an area of interest of the 3D data record is captured.

DESCRIPTION OF THE DRAWINGS

FIGS. 2A and 2B show a region and an enlargement thereof through the virtual channel that proceeds through an organ as well as a blood vessel, FIG. 3 is a flowchart of the method according to the invention.

DESCRIPTION OF THE PREFERRED EMBODIMENTS

Figure 1:
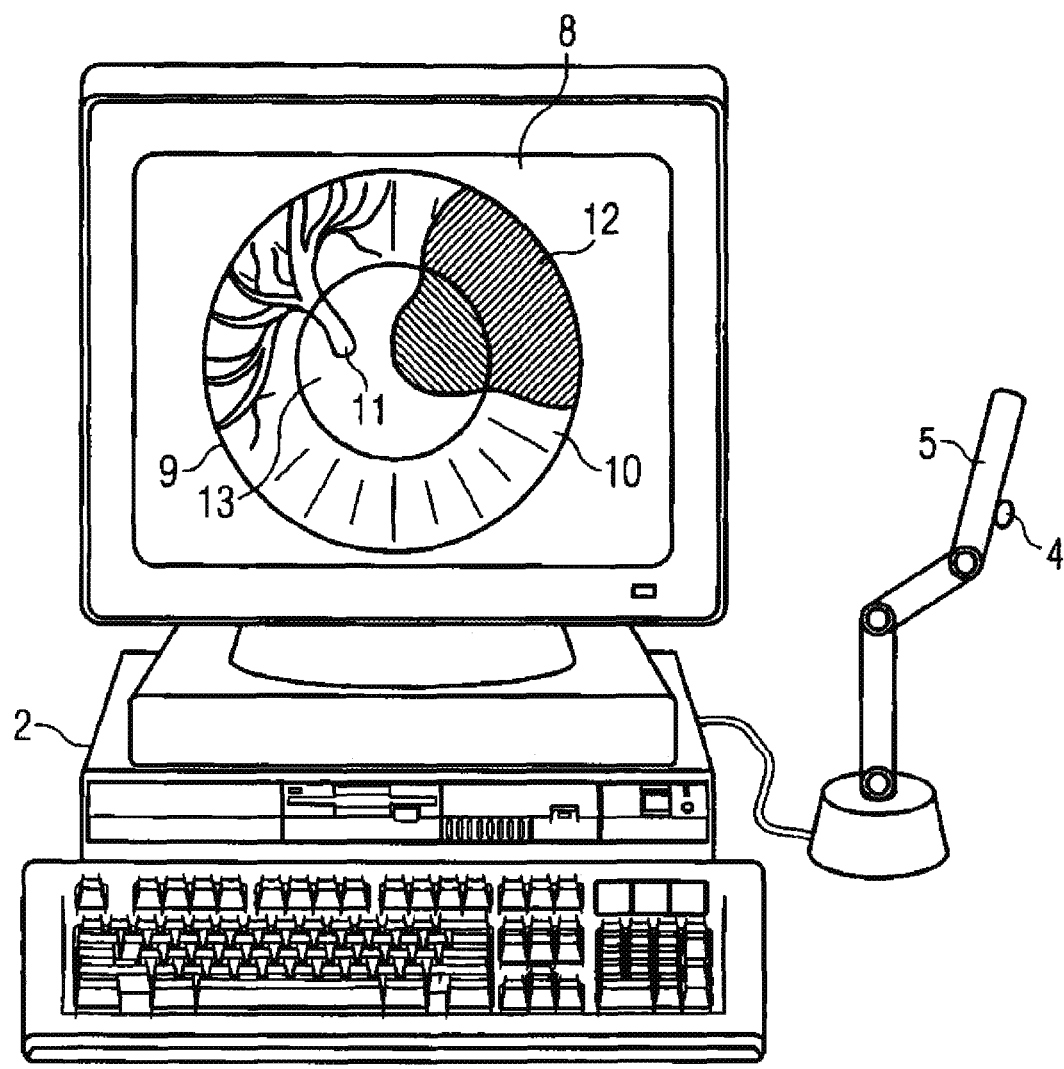
FIG. 1 schematically illustrates the system according to the invention in which an operating or handling system captures the position and orientation of an imaginary (virtual) medical instrument relative to an also virtual or real patient or to a phantom and shows a 3D image of the section of a 3D data record of the patient on the computer, wherein a virtual channel is excised along and in front of the instrument and displayed on the monitor.

FIG. 1 schematically illustrates the basic components of the inventive system for conducting the procedure according to the invention. The basic steps of the procedure according to the invention are shown in FIG. 3 in the form of a flow chart. The most important steps of the procedure according to the invention are steps S2 through S4.

The user has only the 3D data record of the patient 1 to be examined or treated, or additionally the patient 1 to be examined or treated in person, or a similarly dimensioned suitable phantom. Suitable means that the phantom approximately corresponds to the actual patient geometry (thus, in FIG. 2, a phantom can also be provided reference number 1). The 3D data record of the mentioned patient 1 normally is obtained pre-operatively, but can also be obtained intra-operatively with 3D-capable, X-ray devices or 3D-capable ultrasound devices. An operating or handling system 5, which captures the actual position mechanically, electromagnetically, optically, etc., is connected with the computer 2. The system does not have to be coupled mechanically; it can alternatively be a freely moveable rod 3, which simulates a medical measurement field and which e.g. is moved in a magnetic measurement field. With one of these characteristics of the operating system 5, it is possible to excise a virtual optical channel of the 3D data record after a registration of the operating system 5 with respect to the 3D data records based on different channel parameters and independently of the orientation of the operating system 5, and to display the thus-changed 3D data record on the monitor 8 of the computer 2. In order to make the handling of the operating system 5 easier for the user or to make the situation as realistic as possible, a navigation system, can be used, in which a navigation sensor 4 is attached, for example, to the back end of a rod 3, which is supposed to represent the medical instrument (laparoscope, endoscope) to actually be used later, so that the simulated instrument can be moved freely. In another embodiment of the procedure according to the invention, it is also possible to use a medical instrument 3 (laparoscope or endoscope) provided with a navigation sensor 4 and an imaging element (camera) 6. An (access) channel 7 is assigned to the instrument 3, the parameters of which can be set by the user e.g. via the computer 2—in accordance with step S2 in the flow chart diagram in FIG. 3—and the representation of which anticipates which channel will actually be opened when the instrument is pushed ahead further. Possible parameters are the channel diameter, the channel depth, shape of the channel wall (round, square, etc.), shape of the channel base (planar, curved, pointed, etc.) etc.

When moving the instrument 3 toward or placing it on the patient 1 or on the phantom—in accordance with step S1 in the flow chart diagram in FIG. 3—the corresponding channel 7 from the patient-corresponding 3D data record is virtually cut out based on the channel parameters (step 3 in the flow chart diagram). In accordance with step 4 in the flow chart diagram, an artificial and thus virtual channel representation 9 is displayed on the monitor 8 of the computer 2, which ensures a free view of low-lying structures without an actual surgical intervention (e.g. a resection or a biopsy). In this manner, different virtual variants of a possibly difficult surgical operation can be planned interactively and in real time without traumatization by examining the actual patient anatomy.

Of particular importance is the surveillance of the walls 10 of the channel 7, which shows which structures or organs would be transversed when penetrating into the depths of the patient tissue, or cut through in the case of a biopsy or resection. In FIG. 1, a round channel 7, for example, is displayed on the monitor 8 of the computer 2, which cuts a venous or arterial blood vessel 11 and a roundish organ 12 (for example, the liver) as well. The area A, which contains the camera 6 on the tip of the instrument as well as the virtual channel 7, is enlarged in FIG. 2. The organ 12 as well as the venous or arterial vessel 11 is cut virtually. However, based on the specific tissue thickness information from the data record, these e.g. contrast-medium-filled blood vessels or the liver surface within the dynamically relocatable channel could be abandoned, e.g. in order to find a circumvention. At the same time, it is shown how the camera 6 of the instrument 3 would optically capture the channel floor 13 and the channel wall 10 in a later actual operation. However, mainly the virtual channel representation is described below. With the virtual pushing forward of the instrument 3, which either occurs through further "pressing" of the instrument 3 on the patient 1 or the phantom, the channel 7 is lowered further into the inside of the patient. By panning the instrument 3, the channel 7 can be tipped virtually; a virtual lateral offset occurs with lateral parallel displacement. The changing of the instrument position relative to the patient or to the phantom is shown in the flow chart diagram in FIG. 3 as step S5. After changing the instrument position (S5), the channel parameters can be reset or changed. In accordance with step S4, a new excising of the virtual channel takes place based on the new instrument position and as the case may be based on the changed channel parameters. The new channel will finally be shown on the monitor again (S5). The chronology of steps S2 through S5 can be so fast that the channel display on the monitor 8 looks like a movie. In this manner, it is possible to simulate an already described "fly-through technique" as the inspection technique, through which a perspective view of the inner surfaces 10, 13 of the channel and of a surface lying ahead in a definable depth is enabled in each position with a defined objective opening of the camera 6. Within the channel 7, it is possible to leave alone objects such as contrast-medium-filled or self-contrasting objects (e.g. blood vessels 11) in a specific density area so that one can go around them e.g. by varying the instrument 3—i.e. by laterally moving or "wiggling" it. Other structures within the channel can also be shown like "frosted glass," half-transparent and/or in different colors, in order to be able to differentiate each transversed structure. Especially for the "wiggling," the channel diameter can be selected larger than the actual diameter of the instrument used later and the actual instrument diameter or the instrument within the extended channel can be displayed optionally. If the area of interest A is researched or observed sufficiently in a virtual manner, then the procedure is ended with step S6.

As already mentioned, in accordance with the invention, different interactive possibilities (button, mouse click, etc.) are provided to constantly vary the channel image, i.e. for example to shift the position of the channel 7 and to change its orientation, to twist it. For technical reasons (for reasons of compatibility with the real instrument used later and for performance reasons with the available virtual imaging hardware), the cross-sectional form of the channel 7 can also be defined in different manners: circular, elliptical, triangular, rectangular, irregular in any way, etc. As already mentioned, the channel guide along a wiggled path is also provided.

The definition of the channel 7 itself takes place as a calculation based on the 3D data record, based on the channel parameters, as well as based on the instrument position, which was determined by the already mentioned navigation system. In this manner, the user transverses virtually the 3D volume with the instrument (or the sensor 4) in hand. However, in reality, the track of the sensor 4 depending on the channel parameter defines the channel 7. In this sense, the positioning of an instrument is only simulated. The cross-section of the instrument actually used later is projected virtually onto the body surface or in the inside of the body on an organ surface. The determined coordinates of the virtual access channel can then ultimately serve the orientation of the instrument actually used later (e.g. laparoscope). In particular, the combination of the instrument with a controllable robot arm is also possible. With a special arrangement, for example a sensitive mounting of the sensor or the instrument on a mechanical (swing) arm, it is also possible to cause haptic feedback based on the tissue-thickness values of the available 3D data, through which the user gets a feel for the tissue to be transversed. Moreover, a matching of the channel surface with the 3D data can also be performed so that the distance results from the 3D data. With the exact geometrical information, an identical surface of the organ section can be scaled from 3D data according to the instrument image and is matched with it. In this process, for the instrument image, the 3D image is cross-faded with the proper color and transparency selection.

The following exemplary embodiment explains the procedure according to the invention:

A tumor located back on the right lower lob of the liver is to be removed within the framework of a surgical procedure. A preceding laparoscopy is needed, which will first be performed virtually based on the procedure according to invention. There is a three-dimensional preoperative CT image of the stomach area. The organs located under the skin that are to be transversed in the course of the actual laparoscopy later are represented. VR (volume rendering) is used as the basis technology. The uniform thickness value of the blood vessels is colored red. The tumor is selected (e.g. clicked on), for example, from an MPR plane image and colored green in the 3D original data.

According to the later OP instrument (rigid laparoscope), the cross-section of the access channel is made in a curved manner. In order to compare the procedure with actual later conditions, an instrument-like rod with a navigation sensor can be used. The channel itself receives a straight progression in the elongation of the rod or the real instrument. The navigation takes place for example with a magnetic navigation system. A rate action is defined such that first a channel of e.g. 5 cm in length or depth is represented. The user approaches vertically the abdominal wall of the patient or of the phantom with the rod. This is visualized on the monitor of the computer used through a 3D-VR representation of the CT volume. All positions and orientations of the rod or the instrument and thus the navigation sensor are constantly documented in the computer in standardized DICOM coordinates (DICOM standardizes radiological imaging).

When the rod is less than 5 cm from the abdominal wall, a hole based on the rate action is begun to be cut virtually with the defined diameter (trocar point, approx. 1 cm$^2$). Upon continued approach, the whole (the channel) is moved further into the depths. The channel depth can be changed by the user interactively (using button, mouse, etc.). In this way, he can penetrate straight into the depths and thereby thoroughly examine on the channel walls how layers of connective tissue, muscles, intestines, etc. will be transversed, insofar as they are not pushed to the side based on their elasticity. Blood vessels are colored red and possibly left along within the channel, i.e. not cut out. By lateral pushing/moving of the rod and thus the channel, the user is in the position to get by without harming important, large vessels (for example, various blood vessels). Finally, by further advancement, the user reaches the liver, the tissue of which is displayed e.g. like frosted glass for better differentiation, until finally the tumor surface appears in green. The entire green area is circumvented in order to determine coordinates for the subsequent surgical operation (e.g. within the framework of a resection). In the area of the liver, it is particularly important to pay attention to all blood vessels (always shown in red), since the corresponding liver segments would also be sacrificed if these were to be cut.

After obtaining all detailed information, the user retreats again in order to observe the entire channel path with a larger rate action (e.g. 10-15 cm). For this, the user should have the option of continuously variable adjustment of the rate action as well as the option of constantly shifting the virtual width of the channel in order to be able to obtain a more broad illustration. The latter is meaningful because a certain relocatability of the organs in the abdominal area is to be expected. Finally—potentially after several variations and iterations—the user goes back to the initial channel dimension and double-checks the access as the user will optimally implement it.

In actual use, the preoperatively obtained DICOM data is also used. They are for example constantly shown as "target positions" or the difference to the real data is communicated. The control of the instrument via a robot arm is also possible. An alternating display of the preoperative channel image and the actual intra-operative laparoscope image is also possible if an overlay of both images is not desired or implemented.

Although modifications and changes may be suggested by those skilled in the art, it is the intention of the inventor to embody within the patent warranted hereon all changes and modifications as reasonably and properly come within the scope of his contribution to the art.

We claim as our invention:

1. A system for producing a virtual access channel in displayed medical 3D images, comprising:
   a computer containing a pre-operatively-obtained 3D data record of internal anatomy of a patient said computer being configured to reconstruct a 3D virtual image of said internal anatomy from said 3D data record;
   a monitor connected to said computer;
   a position and orientation capturing operating unit connected to said computer that is manually manipulable to simulate a movement and a position of a medical instrument, said operating unit generating and emitting an operating unit output signal that represents said simulated position and simulated movement; and
   said computer being supplied with said operating unit output signal and producing a registration between the simulated position and simulated movement represented by said operating unit output signal and the internal anatomy of the patient in said 3D data record and thus in said 3D virtual image of said internal anatomy, and said computer continuously excising a virtual optical channel in said 3D virtual image of said internal anatomy of the patient in real time and interactively with the manual manipulation of said position and orientation capturing operating unit, based on said registration and based on at least one channel parameter selected from the group consisting of a channel diameter, a channel depth, a shape of a channel wall, and a shape of a channel base and entered into said computer via said operating unit, and displaying, on said monitor, said virtual 3D image of said internal anatomy with said excised virtual optical channel therein as a perspective virtual fly-through of said internal anatomy along said optical channel.

2. A system as claimed in claim 1 wherein said operating unit comprises a unit selected from the group consisting of a mechanically articulated system, a navigation system, a rod-shaped medical instrument with a navigation sensor, an optical marking of a computer input system, and a magnetic marking of a computer input system.

3. A system as claimed in claim 1 wherein said computer leaves selected vessels or organs in said 3D data record undisturbed in said virtual channel for causing said selected vessels or organs to be displayed on said monitor within said channel or extending into said channel.

4. A system as claimed in claim 1 wherein said 3D data record contained in said computer is a data record selected from the group consisting of a magnetic resonance tomography 3D data record, a computed tomography 3D data record, an ultrasound 3D data record, a positron emission tomography 3D data record, and a 3D data record obtained by a nuclear medicine procedure.

5. A system as claimed in claim 1 wherein said computer automatically excises said virtual optical channel by a computation employing an algorithm.

6. A system as claimed in claim 1 wherein said computer additionally causes a representation of said medical instrument to be displayed in said virtual channel.

7. A system as claimed in claim 6 comprising a second position and orientation capturing operating unit that identifies a position and an orientation of said instrument, and wherein said computer illustrates movement of the virtual channel and the representation of the medical instrument independently, using respective information from said position and orientation capturing operating unit and said second position and orientation capturing operating unit.

8. A system as claimed in claim 1 wherein said operating unit is a robot arm.

9. A system as claimed in claim 1 wherein said operating unit is a mechanically articulated system producing information for generating haptic feedback in said computer, additionally based on a tissue thickness map of said 3D data record.

10. A system as claimed in claim 1 wherein said computer displays said image of said virtual channel together with corresponding intra-operatively obtained real-time images.

11. A system as claimed in claim 10 comprising a real-time imaging system for obtaining said intra-operative real-time images, selected from the group consisting a laproscope, a colonscope, and endescope and an ultrasound system.

12. A method for producing a virtual access channel for a medical instrument in a displayed image, comprising the steps of:
   pre-operatively obtaining a 3D electronic data record representing internal anatomy of a patient, and supplying 3D data record to a computer having a monitor and, in said computer, reconstructing a 3D virtual image of said internal anatomy from said 3D data record;
   manually manipulating a position and orientation capturing operating unit that is connected to said computer to simulate a movement and a position of a medical instrument and, in said operating unit, generating and emitting an operating unit output signal that represents said simulated position and simulated movement;
   with said operating unit, designating at least one channel parameter selected from the group consisting of a channel diameter, a cannel depth, a shape of a channel wall, and a shape of a channel base, and supplying said at least one channel parameter and said operating unit output signal to said computer;
   in said computer, producing a registration between the simulated position and simulated movement represented by the operating unit output signal and the internal anatomy of the patient in said 3D data record and thus in said 3D virtual image of said internal anatomy, and continuously excising a virtual optical channel in 3D virtual image of said internal anatomy of the patient in real time and interactively with the manual manipulation of said position and orientation capturing operating unit, based on said registration and based on said at least one channel parameter; and
   from said computer, causing said 3D virtual image of said internal anatomy to be displayed on said monitor therein as a perspective virtual fly-through of said internal anatomy along said optical channel.

13. A method as claimed in claim 12 comprising employing a unit, as said operating unit, selected from the group consisting of a mechanically articulated system, a navigation system, a rod-shaped medical instrument with a navigation sensor, an optical marking of a computer input system, and a magnetic marking of a computer input system.

14. A method as claimed in claim 12 comprising in said computer leaving selected vessels or organs in said 3D data record undisturbed in said virtual channel for causing said selected vessels or organs to be displayed on said monitor within said channel or extending into said channel.

15. A method as claimed in claim 12 comprising employing a data record, as said 3D data record, selected from the group consisting of a magnetic resonance tomography 3D data record, a computed tomography 3D data record, an ultrasound 3D data record, a positron emission tomography 3D data record, and a 3D data record obtained by a nuclear medicine procedure.

16. A method as claimed in claim 12 comprising in said computer automatically excising said virtual optical channel by a computation employing an algorithm.

17. A method as claimed in claim 12 comprising in said computer additionally causing a representation of said medical instrument to be displayed in said virtual channel.

18. A method as claimed in claim 17 comprising employing a second position and orientation capturing operating unit that identifies a position and an orientation of said instrument, and in said computer illustrating movement of the virtual channel and the representation of the medical instrument independently, using respective information from said position and orientation capturing operating unit and said second position and orientation capturing operating unit.

19. A method as claimed in claim 12 comprising employing a robot arm as said operating unit.

20. A method as claimed in claim 12 comprising employing a mechanically articulated system as said operating unit and therewith producing information for generating haptic feedback in said computer, additionally based on a tissue thickness map of said 3D data record.

21. A method as claimed in claim 12 comprising displaying said image of said virtual channel together with corresponding intra-operatively obtained real-time images.

22. A method as claimed in claim 21 employing a real-time imaging system for obtaining said intra-operative real-time images, selected from the group consisting a laproscope, a colonscope, and endescope and an ultrasound system.

23. A method as claimed in claim 12 comprising producing said registration of said operating unit relative to said 3D data record using a navigation system.

* * * * *